(12) United States Patent
Page

(10) Patent No.: US 8,481,931 B2
(45) Date of Patent: Jul. 9, 2013

(54) ELECTRON SPECTROSCOPY

(75) Inventor: Simon Page, Hadfield (GB)

(73) Assignee: Kratos Analytical Limited, Manchester (GB)

( * ) Notice: Subject to any disclaimer, the term of this patent is extended or adjusted under 35 U.S.C. 154(b) by 438 days.

(21) Appl. No.: 12/482,577

(22) Filed: Jun. 11, 2009

(65) Prior Publication Data
US 2009/0309023 A1 Dec. 17, 2009

Related U.S. Application Data

(60) Provisional application No. 61/129,206, filed on Jun. 11, 2008.

(30) Foreign Application Priority Data

Jun. 11, 2008 (GB) .................................. 0810723.7

(51) Int. Cl.
*G21K 5/00* (2006.01)
*H01J 37/26* (2006.01)

(52) U.S. Cl.
USPC ........... 250/306; 250/305; 250/307; 250/281; 250/282; 250/287; 250/492.1; 250/492.3

(58) Field of Classification Search
USPC ................. 250/305, 306, 307, 281, 282, 287, 250/492.1, 492.3
See application file for complete search history.

(56) References Cited

U.S. PATENT DOCUMENTS

| 5,619,035 | A | | 4/1997 | Weiss et al. |
| 5,877,496 | A | * | 3/1999 | Tabuse et al. ................. 250/288 |
| 6,265,722 | B1 | | 7/2001 | Marsh |
| 6,268,608 | B1 | * | 7/2001 | Chandler ................... 250/492.2 |
| 6,395,347 | B1 | | 5/2002 | Adachi et al. |
| 2002/0028289 | A1 | * | 3/2002 | Veerasamy ................ 427/249.7 |
| 2003/0161970 | A1 | | 8/2003 | Kaito |
| 2004/0238735 | A1 | * | 12/2004 | Larson et al. ................. 250/281 |
| 2006/0097193 | A1 | * | 5/2006 | Horsky et al. ............ 250/492.21 |
| 2008/0105828 | A1 | * | 5/2008 | Hatem et al. ................... 250/426 |
| 2010/0197142 | A1 | * | 8/2010 | Randolph et al. ............. 438/710 |

FOREIGN PATENT DOCUMENTS

| EP | 1 679 505 A1 | 7/2006 |
| JP | 2005-134170 A | 5/2005 |
| WO | WO 2007/080594 A2 | 7/2007 |

OTHER PUBLICATIONS

Daniel Weibel et al., "A C60 Primary Ion Beam System for Time of Flight Secondary Ion Mass Spectrometry: Its Development and Secondary Ion Yield Characteristics", Anal. Chem. 2003, pp. 1754-1764.
Gregory X. Biddulph et al., "Properties of C84 and C24H12 Molecular Ion Sources for Routine TOF-SIMS Analysis", Anal. Chem. 2007, pp. 7259-7266.
Extended European Search Report corresponding to European Patent Application No. 09251534.5 dated Sep. 26, 2011.

* cited by examiner

*Primary Examiner* — Nicole Ippolito
(74) *Attorney, Agent, or Firm* — Squire, Sanders (US) LLP

(57) ABSTRACT

The present invention provides an electron spectroscopy apparatus (12) comprising a high energy particle source (12) for irradiating a sample, an electron detector system (16) (e.g. including a delay line detector) for detecting electrons emitted from the sample and an ion gun (8) for delivering a polycyclic aromatic hydrocarbon (PAH) ion beam to the sample, wherein the ion gun comprises a polycyclic aromatic hydrocarbon ion source, for example comprising coronene. In an embodiment, the PAH is located in a heated chamber (22) and vaporised to produce gas phase PAH. The gas phase PAH molecules are then ionised by electron impact, extracted from the ion source via an extraction field and focussed using ion optics. The PAH ion beam can be used for surface cleaning and depth analysis.

24 Claims, 4 Drawing Sheets

ELECTRON SPECTROSCOPY

CROSS-REFERENCE TO RELATED APPLICATION

This application claims the benefit of U.S. Provisional Application No. 61/129,206 filed on Jun. 11, 2008, which is hereby incorporated by reference.

BACKGROUND OF THE INVENTION

The present invention is concerned with electron spectroscopy and apparatus for performing electron spectroscopy. In particular, the present invention is concerned with ion sources for electron spectroscopy, which ion sources can be used to selectively remove surface layers from a sample prior to analysing the sample.

Electron spectroscopy is primarily a surface analysis technique wherein the surface of a sample is bombarded with high energy particles causing electrons to be emitted from the sample via the photoelectric effect. When the bombarding high energy particle is an x-ray, the technique is known as x-ray photoelectron spectroscopy (XPS); when the high energy particle is UV radiation, the technique is known as photoemission spectroscopy (PES) or ultra-violet photoemission spectroscopy (UPS). Bombardment and detection of emitted electrons takes place under ultra high vacuum conditions. The technique is also known as photoelectron spectroscopy. Analysis of the kinetic energy and number of emitted electrons allows information regarding the composition and bonding within the sample to be deduced.

Thus, electron spectroscopy allows an elemental composition to be measured but also provides a means of deducing the chemical environment of each element. In particular, the exact position of each peak in the spectrum can be analysed to ascertain bonding information. Where an element is bonded in different ways to the same or other elements a "peak envelope" is formed. A peak envelope comprises a number of partially overlapping peaks. Analysis of this peak envelope permits a deduction of the types of bonds and relative proportion of them, thereby revealing information regarding the chemical composition of the sample It can also be helpful to obtain information about the distribution of elements in the sample, in particular the change in composition as a function of distance from the surface. Where such a depth analysis is to be performed it is necessary to remove the overlying layers so as to expose an underlying layer for analysis. Importantly, any technique for removing the outer layer should not damage the underlying layer otherwise analysis of the underlying layer will be compromised.

Conventionally, an ion beam is used to remove outer layers. Suitably the ion beam will have a high sputter yield, meaning that unwanted material is removed from the surface as quickly as possible with the minimum ion dose.

Electron spectroscopy apparatus comprises a sample stage, high energy particle source and detector for detecting emitted electrons. The apparatus suitably also includes electron focusing optics to direct the emitted electrons onto the detector. Many apparatuses also comprise an ion source which produces ions that are directed onto the surface of the sample to remove unwanted material from the surface of the sample prior to analysis. Ions that have been used to clean the surface of the sample include argon ions and C60 ions.

Argon ions, while effectively removing material from the surface of a sample, can cause surface damage. This can have detrimental affect on the subsequent analysis of the sample. C60 ions are also known to remove material from the surface of a sample and, depending on the sample, may exhibit reduced surface damage as compared to argon ions (EP 1 679505 A1). However, it has also been observed that sputtering with C60 can result in the formation of a "false layer" as a result of the deposition of C60 on the surface. This limits the usefulness of C60 as an ion source and can lead to misleading results.

The present invention seeks to address the drawbacks associated with known ion beams. In particular, the present invention seeks to address the problem of removing outer layers of material as quickly and efficiently as possible, while minimizing damage to underlying layers and preserving the chemical environment of the elements within the sample. A further problem addressed by the invention is to remove material from an outer layer while minimizing the deposition of "foreign" material onto or into the sample.

At its most general, the present invention proposes that polycyclic aromatic hydrocarbons should be used as an ion source for removing material from an outer layer of a sample. The present inventor has found that polycyclic aromatic hydrocarbons provide improvements in terms of reduced sample damage and deposition of unwanted material compared to conventional ion sources, in particular argon and C60 ion sources.

In a first aspect, the present invention provides electron spectroscopy apparatus comprising a high energy particle source for irradiating a sample, an electron detector system for detecting electrons emitted from the sample and an ion gun for delivering a polycyclic aromatic hydrocarbon ion beam to the sample, wherein the ion gun comprises a polycyclic aromatic hydrocarbon ion source.

The present inventor has found that polycyclic aromatic hydrocarbons (PAHs) can efficiently remove material from the surface of a sample. Indeed, embodiments of the invention demonstrate high sputtering levels, meaning that significant amounts of surface material can be removed using comparatively small numbers of PAH ions. Furthermore, experiments conducted by the present inventor show that surface cleaning or etching can be achieved without causing significant damage to underlying layers. A further surprising observation is that PAH ions, despite their efficiency in removing material from the surface, do not themselves tend to become deposited on the surface. The problem of "false layers" and contamination of underlying layers is therefore minimized or avoided in embodiments of the present invention.

These advantages associated with the use of PAH ions enables a more accurate determination of the composition of a sample using electron spectroscopy.

Preferably the PAH comprises 5 to 20 aromatic rings, more preferably 5 to 15 aromatic rings, more preferably 5 to 10 aromatic rings and most preferably 6 to 8 aromatic rings. A particularly preferred group of PAH comprises 7 aromatic rings.

Preferably the PAH is unsubstituted.

An especially preferred PAH is coronene ($C_{24}H_{12}$). Coronene has been found to be particularly effective at surface cleaning and etching, while minimizing damage or contamination of underlying layers.

Another preferred PAH related structurally to coronene is dicoronylene, which is the dimer of coronene. It is expected that dicoronylene would behave in a similar manner to coronene because of fragmentation of dicoronylene. If necessary, and as discussed below, unwanted fragments could be removed by a filter, for example a Wien filter.

Other preferred examples of PAH include anthracene, pyrene, coronene, and ovalene. Without wishing to be bound by theory, the present inventor believes that the compact structure of the fused rings of PAH is responsible for the unexpected advantages associated with PAHs as an ion source. The compact structure means that a significant number of impacting atoms are concentrated into a small region of the sample surface. Furthermore, the present inventor believes that the open, and generally planar, aromatic carbon structure of PAHs means that the energy is evenly spread over the impact area. This enables the penetration depth to be controlled, leading to more accurate cleaning or surface layer removal.

Suitably the ion source comprises (i) a gas generator wherein gas phase molecules of PAH are produced; (ii) an ioniser wherein the gas phase molecules of PAH are ionised.

Preferably the gas generator comprises a heated chamber (for example, an oven). Suitably this enables the PAH to be vaporised. Preferably the heated chamber is adapted to operate at a temperature in the range 100° C. to 300° C.

Preferably the ioniser comprises an electron impact ioniser whereby PAH ions are created by bombardment of PAH gas phase molecules with electrons.

Thus, the ion source preferably comprises a heated chamber and an electron impact ioniser.

Preferably the ion gun includes gas supply means to deliver gas to the ioniser. Preferably the gas is selected from Ar, $O_2$ and $SF_6$.

Suitably the ion gun includes one or both of (iii) an ion extractor and (iv) ion optics. Preferably the ion extractor accelerates ions away from the ion source. Preferably the ion optics focus and/or align the ions.

Suitably the ion gun also includes one or both of (v) a mass filter (suitably a Wien filter) and (vi) an ion separator. Preferably the mass filter permits ions of a desired mass or masses to proceed to the sample, but prevents passage of ions of other masses. Preferably the ion separator removes neutral species, leaving only charged species.

The ion gun may also include (vii) a second ion optics, to focus ions after mass filtering and/or ion separation. For example the second ion optics can be an objective lens.

The ion gun suitably includes (viii) an ion scanner. Suitably the ion scanner directs the ions onto different areas of the sample. Preferably the ion scanner directs the ions onto a target area of the sample, wherein the target area moves so that different ions are directed at different locations on the sample surface. Suitably the ion scanner provides a raster pattern across the sample, for example a square or rectangular pattern. An ion scanner is preferred because "scanning" of the ions produces a more uniform distribution of current on the specimen so as to produce a rate of material removal which depends minimally on the position within the analysis area of the apparatus.

Thus, preferably the apparatus is configured to produce ionised PAH molecules, which are then extracted focussed, aligned, mass filtered, separated from the electrically neutral molecules, further focussed and scanned across the sample.

Preferably the apparatus includes an ion beam controller for switching between first (PAH) and second (gas) ion beam modes.

Preferably the ion source includes PAH. Preferably it includes coronene. Suitably the PAH is in the form of a pre-form, typically formed by compressing PAH. In embodiments the PAH may also be provided as a fibrous solid (for example coronene having a fibrous crystalline structure can be loaded into the ion source)

Suitably the ion gun is adapted to provide ions of different charge states. In other words, the ion gun can apply different charges to an ion, for example 1+, 2+, etc. Suitably, the ion gun includes a Wien filter and the Wien filter can be set to transmit different charges of an ion. This is useful because it enables higher impact energy to be achieved for a particular ion accelerating voltage. For example a 2+ charged ion accelerated through a potential difference of 10 kV acquires a kinetic energy of 20 keV.

Preferably the electron detector system includes an electron energy analyser. Suitably the electron energy analyser includes a hemispherical analyser. Alternatively or additionally the electron energy analyser includes a spherical mirror analyser. Preferably the electron detector system includes an electron analyser as described in patent GB2244369, which electron analyser comprises a spherical mirror analyser and a hemispherical analyzer.

Suitably the electron detector system includes a channeltron or microchannel plate electron detector.

Preferably the electron detector system includes a detector, suitably a delay line detector.

Suitably the apparatus includes a vacuum chamber, suitably an ultra-high vacuum chamber. Preferably the sample and/or electron detector system are located within the vacuum chamber.

Preferably the step of detecting electrons includes detecting the kinetic energy and/or detecting the number of electrons, preferably both.

Preferably the apparatus is an XPS apparatus or a PES apparatus, preferably an XPS apparatus.

In a second aspect, the present invention provides an electron spectroscopy method, the method including the steps of irradiating a sample with high energy particles and detecting electrons emitted from the sample, wherein the method includes the step of directing a polycyclic aromatic hydrocarbon ion beam onto the sample.

Preferably the PAH ion beam has an energy of between 2 and 20 keV, preferably 5 to 15 keV.

Preferably the PAH vapour to be ionised for the ion beam is generated by heating the PAH, suitably to a temperature in the range 150° C. to 300° C., preferably approximately 200° C. for the case of coronene. Other PAHs will require different temperatures in order to achieve a vapour pressure in the correct range for the ion beam current required.

Suitably the method includes the step of removing a surface layer of material from the sample with the PAH ions. Preferably the method involves repeatedly removing a surface layer of material from the sample with PAH ions.

Preferably the method includes the step of cleaning the surface of a sample with PAH ions.

Preferably the high energy particles are photons. Suitably the photons are selected from x-rays and UV radiation.

More generally, the apparatus can be used to perform electron spectroscopic surface analysis and sputter depth profiling in the same way as conventional electron spectrometer apparatus.

In a third aspect, the present invention provides a polycyclic aromatic hydrocarbon ion gun for use in an apparatus of the first aspect.

Suitably the ion gun is adapted to be used with PAHs and gases. In other words, the ion gun is preferably configured so that gases such as argon, other noble gases, oxygen, $SF_6$ can be used to produce an ion beam, as well as being adapted to produce a PAH ion beam.

Suitably the ion gun is as defined in the first aspect.

Preferably the ion gun includes a heated chamber for producing gas phase PAH; an ioniser for ionising the gas phase PAH; and gas supply means for delivering a room temperature gas to the ioniser.

In a fourth aspect, the present invention provides a use of a polycyclic aromatic hydrocarbon in a method of analysing a sample by electron spectroscopy.

In a fifth aspect, the present invention provides a use of a polycyclic aromatic hydrocarbon in a method of making an apparatus of the first aspect.

In a sixth aspect, the present invention provides a use of a polycyclic aromatic hydrocarbon in a method of making an ion gun of the third aspect.

In a seventh aspect, the present invention provides a method of modifying an electron spectrometer apparatus so that it can perform a method of the second aspect.

Suitably the method of modifying an electron spectrometer apparatus includes the step of providing the apparatus with a polycyclic aromatic hydrocarbon ion gun of the third aspect.

Any one or more of the aspects of the present invention may be combined with any one or more of the other aspects of the present invention. Similarly, any one or more of the features and optional features of any of the aspects may be applied to any one of the other aspects. Thus, the discussion herein of optional and preferred features may apply to some or all of the aspects. In particular, optional and preferred features relating to the apparatus of the present invention may also apply to the methods and uses of the present invention, and vice versa.

As used herein, the terms "polycyclic aromatic hydrocarbon" and "PAH" mean a chemical compound composed of fused aromatic hydrocarbon rings. The skilled reader is familiar with the terms and the members of the chemical family of PAH. Examples of PAH include anthracene ($C_{14}H_{10}$; three fused benzene rings), pyrene ($C_{16}H_{10}$; four fused benzene rings), coronene ($C_{24}H_{12}$; seven fused benzene rings), and ovalene ($C_{32}H_{14}$; ten fused benzene rings).

The invention will now be described by way of example only with reference to the accompanying figures in which.

The present inventor has found that various PAHs (polycyclic aromatic hydrocarbons) provide a particularly effective ion source for surface cleaning and depth analysis for electron spectroscopy and x-ray electron spectroscopy (XPS) in particular. PAHs have been found to provide high sputter yields and minimal damage and, unlike other ion sources (for example C60), appear to have a reduced tendency to deposit on the sample (produce a false composition).

A further advantage of PAHs is that they can be vaporised comparatively easily. Indeed, many PAHs have a relatively high vapour pressure and therefore may be readily induced in the vapour state by slight heating. This means that a lower temperature and hence less energy is required in order to vaporize PAH as compared to for example C60. The ion generator of the ion source can therefore be a relatively low power heated chamber (oven).

Not only is less energy needed to produce PAH ions, but a lower oven temperature causes fewer problems when operating the ion source as compared to higher temperature ovens. It is well known that many electrically insulating materials become less insulating at high temperatures and so can conduct away the high voltages needed to accelerate the ions from the ion generator. This can lead to difficulties in providing the required high voltages from the power supply.

Furthermore, many materials used in the construction of ion sources and ion optical components "outgas" at high temperatures leading to additional, unwanted gases in the ion generator. These unwanted ions must be separated from the desired ions otherwise they would be transported to the sample and cause damage to the specimen in a similar manner to that caused by for example noble gas ions.

Figure 1:
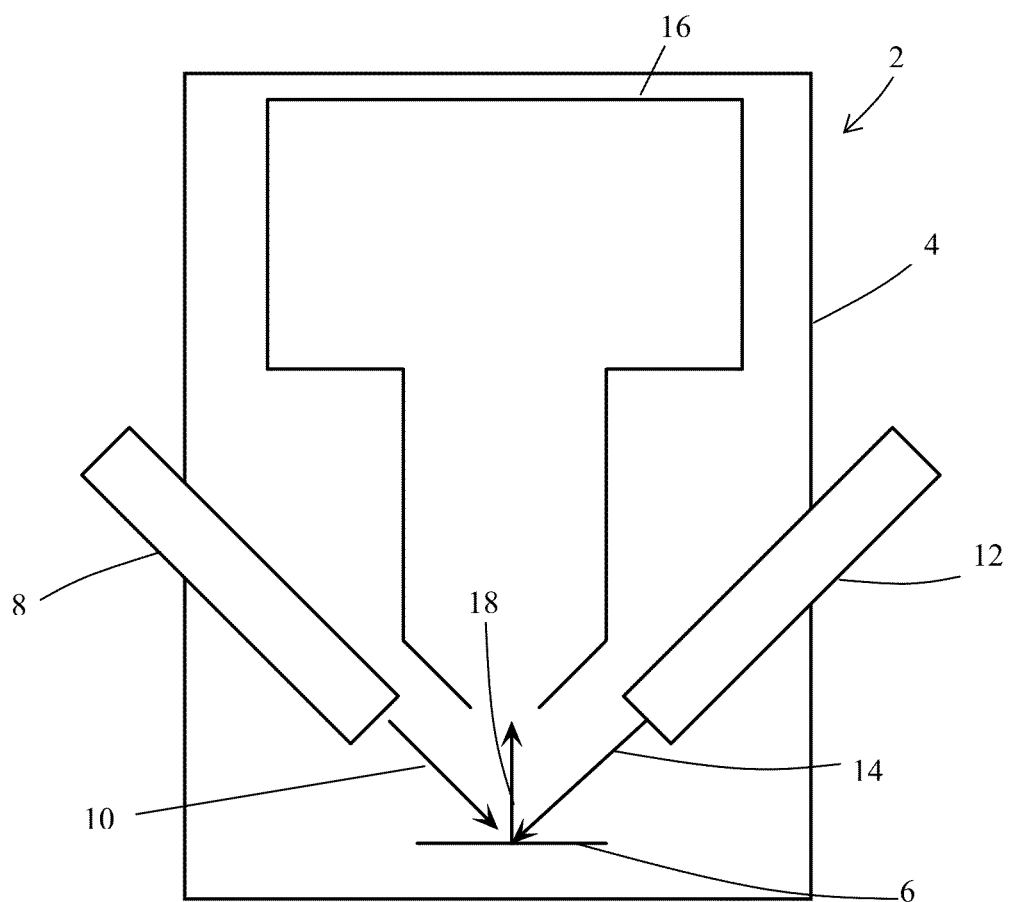
FIG. 1 shows a schematic illustration of an apparatus of the present invention.

FIG. 1 is a schematic illustration of an electron spectroscopy apparatus 2 according to the present invention. The apparatus comprises an ultra-high vacuum enclosure 4, in which sample stage 6 is located. An ion gun 8 extends into the ultra-high vacuum enclosure 4 and provides a PAH ion beam 10 which is directed to the sample on the sample stage during use.

Photon source 12 is arranged so as to provide a photon beam 14 incident on the sample during use. Within the vacuum enclosure 4 is photoelectron spectrometer 16, which detects electrons 18 emitted from a sample in use.

The photon source 12 and photoelectron spectrometer 18 can be conventional and the skilled reader is familiar with appropriate examples.

The photoelectron spectrometer includes electron lenses (not shown) for collecting and focussing the photoelectrons. It also includes an energy dispersive analysing device, which in this embodiment is a concentric hemispherical analyser. The photoelectron spectrometer also includes an electron detection system. The electron detection system comprises a detector for detecting emitted electrons. In this embodiment the detector is a microchannel plate with a delay line detector readout and the photoelectron spectrometer also includes a spherical mirror analyser and a hemispherical analyzer. However, other analyzers and detectors (for example a channeltron) can be used.

The various components of the photoelectron spectrometer are controlled from a computer controlled power supply system and data acquisition system.

The photon source 12 can be any of a gas discharge source able to produce photon in the ultraviolet energy range, an x-ray source based on electron impact on a metallic target so as to produce a characteristic x-ray line such as Mg Kα or Al Kα placed in close proximity to the sample to be analysed, or photons from an x-ray monochromator or synchrotron radiation source. In the embodiment shown in FIG. 1, the photon source is an x-ray source, which is preferred.

Figure 2:
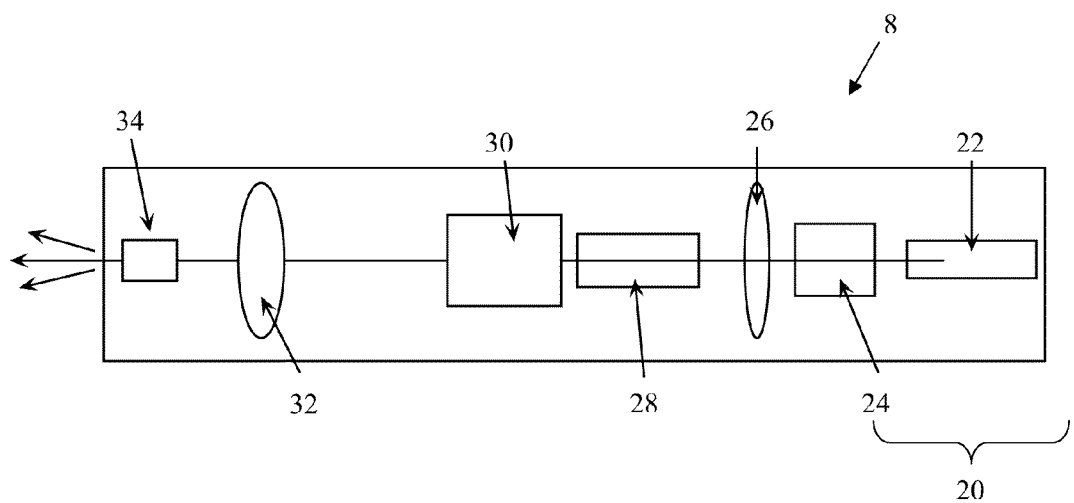
FIG. 2 shows a schematic illustration of an ion gun of the present invention.

FIG. 2 illustrates schematically the ion gun 8 of FIG. 1. The ion gun 8 includes an ion source 20 comprising a heated chamber 22 and an electron impact ioniser 24. PAH is located in the heated chamber and vaporised to produce gas phase PAH. The gas phase PAH molecules that effuse into the ioniser are then ionised by electron impact in the electron impact ioniser 24. The PAH ions are then extracted from the ion source via an extraction electric field and focussed and aligned using ion optics 26.

The PAH ions are then mass filtered by passing the ions through a Wien filter 28 to select ions of a particular velocity. The desired ions (electrically charged molecules) are then separated from electrically neutral molecules with a neutral filter 30. The filtered PAH ions are then further focussed by objective lens 32 and scanned across the specimen using scanning plates 34. The step of scanning the PAH ions across the sample is performed to produce a more uniform distribution of current on the specimen. This has the advantage that the rate of material removal from the sample depends minimally on the position of the material within the analysis area of the photoelectron spectrometer.

As is generally preferred, the ion gun is adapted to operate with both PAH and gas sources such as Ar. In particular, the gun is configured to operate equally well with PAH at high energy, for example up to 20 keV, and with Ar at low energy, for example approximately a few 10 eV. When the gun is operated in the low energy mode with Ar, the heated chamber (oven) 22 is not activated and Ar is supplied ("leaked") to the ioniser 24. The Ar ion energy can be kept at a few keV through the main part of the gun and then retarded to the required low energy through the objective lens 32. This allows higher current densities to be achieved at low energy. When combined with PAH mode operation the ion gun represents a very valuable contribution to electron spectroscopy.

Suitably the ion gun includes gas supply means to deliver gas (i.e. molecules that are a gas at room temperature) to the ioniser (e.g. in the "gas mode"). Suitably the gas is selected from Ar, $O_2$ and $SF_6$.

Suitably the apparatus include an ion beam controller for switching between first (PAH) and second (gas) modes of operation. Preferably the ion beam controller is a computer or other control device used to control the ion gun.

In the embodiment shown in FIG. 2, the heated chamber 22 includes PAH. The heated chamber 22 can be loaded with additional PAH as required.

A particular advantage of PAHs is that the steps outlined above needed in order to produce an ion beam are readily achieved. Indeed, the production of a PAH ion beam may be considerably more energy efficient and technically less complicated than for C60. This can bring about significant advantages when the PAH ion gun is used in practice, both in terms of equipment maintenance, ease of use and overall efficiency.

Figure 3:
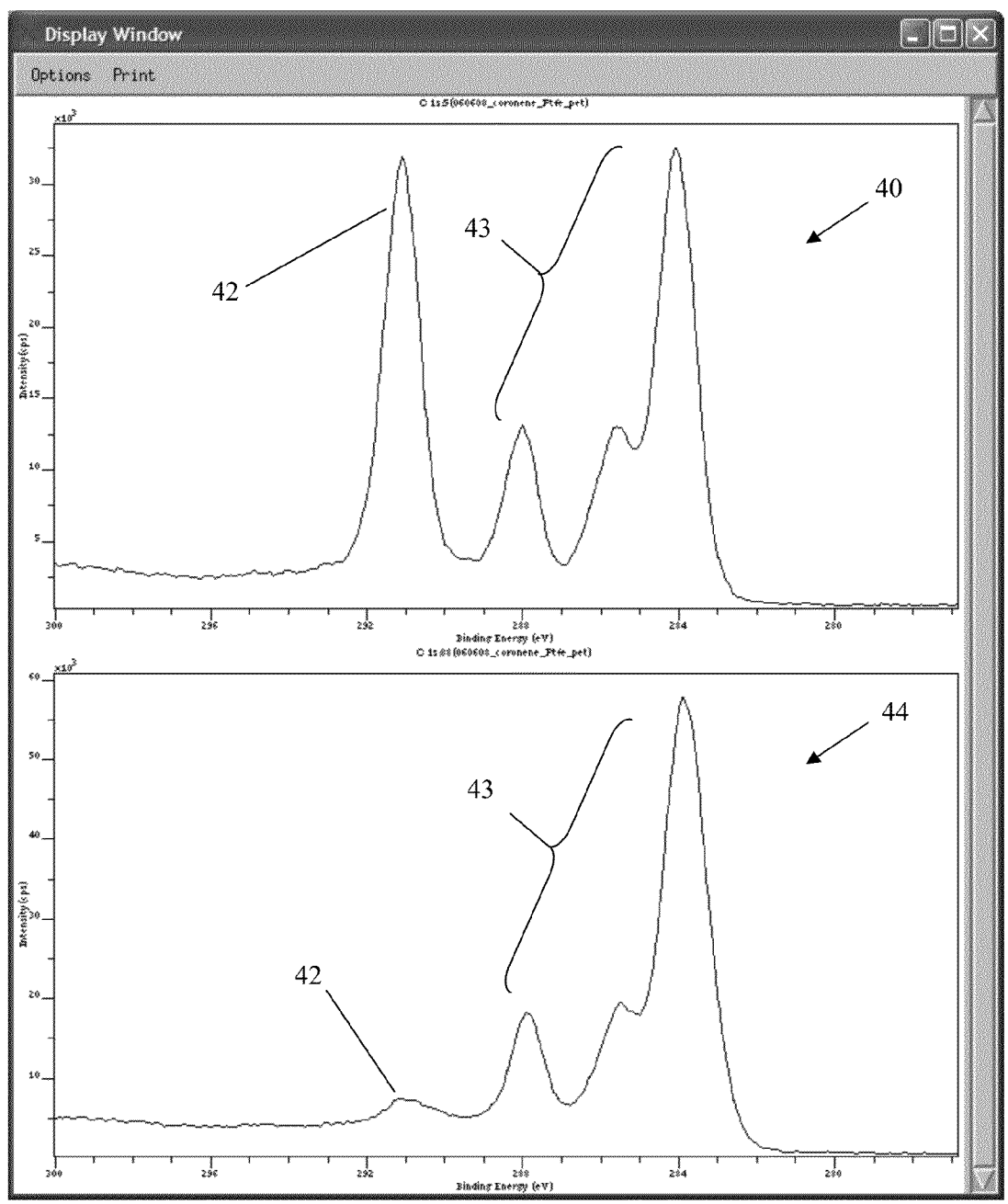
FIG. 3 shows spectra obtained from a PET sample that has been contaminated with PTFE that is subsequently cleaned off using a PAH ion source of the present invention.
Figure 4:
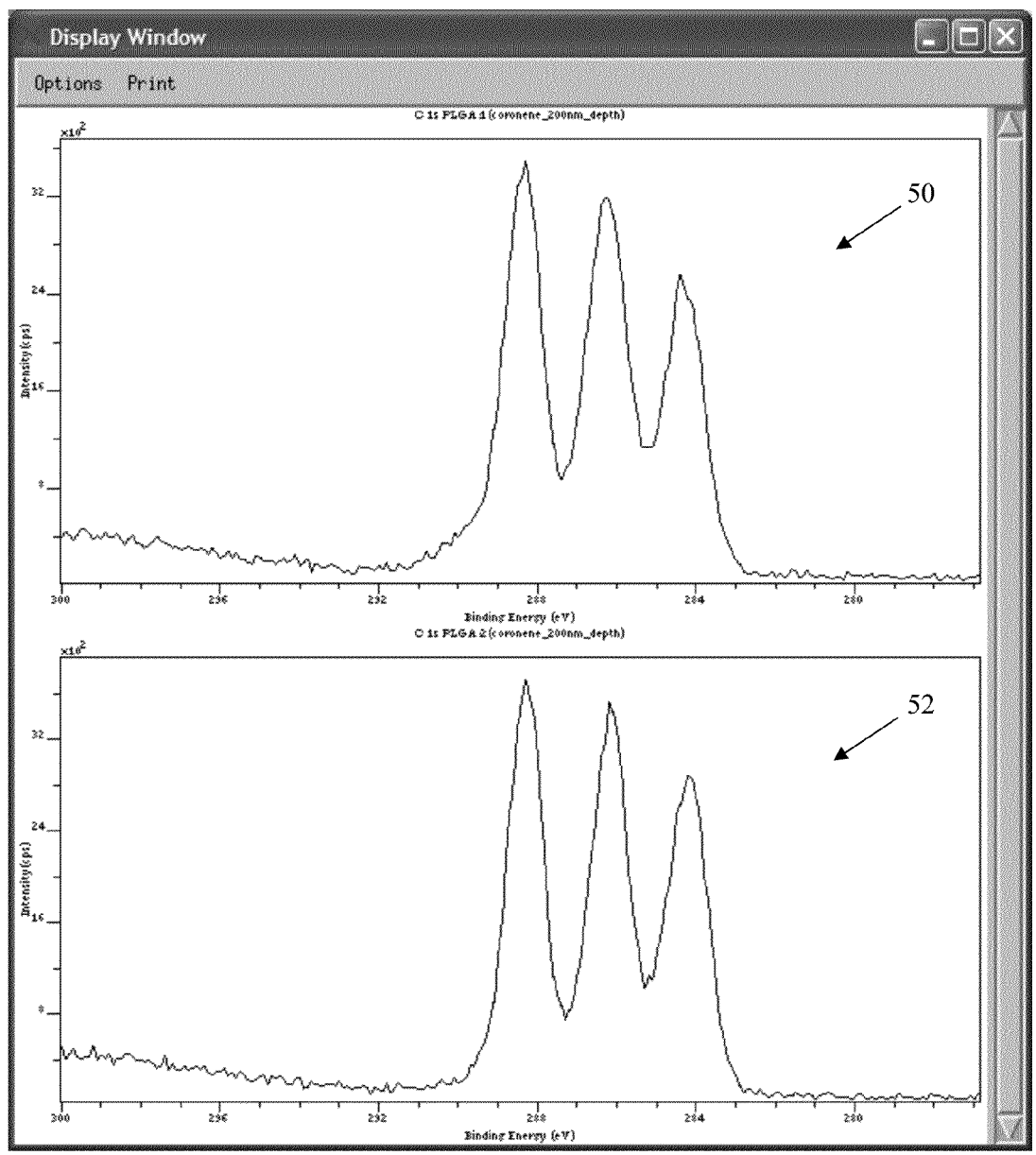
FIG. 4 shows spectra obtained from a PLGA sample using a PAH ion source of the present invention before and after removal via PAH sputtering of 200 nm of material.

The spectra shown in FIGS. 3 and 4 were obtained using a Kratos AXIS Ultra apparatus adapted so that the ion gun included PAH as discussed above with respect to FIG. 2.

In order to obtain the XPS spectra, the PAH (coronene) was placed in a temperature controlled heated cell and induced into the vapour state by heating. The vapour was ionised via electron impact in the ioniser and directed via electrostatic fields into the condenser lens which focused and controlled the ion beam current. The ions then passed through the Wien filter which passes along its axis ions of a particular velocity. Un-ionised neutral molecules were separated out of the beam in the neutral filter. The objective lens then focused the filtered ions into a small spot which was then scanned across the sample in a pattern appropriate to the area required to be analysed, typically a square or rectangular pattern.

FIG. 3 shows two XPS spectra obtained from analysis of a sample comprising a PTFE layer applied to a polyethylene terephthalate (PET) substrate. Specifically, the PET substrate has been mechanically smeared with a layer of PTFE.

The operating conditions used to acquire the spectra are as follows: an AlKα x-ray monochromator operated at a power of 150 W, an analysis area of 110 microns and a hemispherical analyser pass energy of 40 eV.

The upper trace 40 shows the C 1 s region of the spectrum which has a chemically shifted peak 42 at a binding energy of 291 eV characteristic of the —$CF_2$ bond in PTFE in addition to the well known characteristic spectrum from the PET underlayer 43.

The lower trace 44 was obtained after sputtering for 600 s with 12 keV coronene ($C_{24}H_{12}^+$). As can be seen from the spectrum, the —$CF_2$ peak 42 has almost disappeared while the characteristic spectrum from PET remains virtually unchanged.

Importantly, there is no evidence in the spectrum of any contamination or false layer formation by the coronene ion beam. This result demonstrates that coronene is effective at cleaning the surface of the sample (removing an upper layer) whilst preserving the composition and structure of the underlying layer(s) and avoiding contamination of the sample.

FIG. 4 shows two further XPS spectra. These were obtained from a sample comprising a silicon wafer coated with a thin layer of poly(lactic-co-glycolic acid) (PLGA). The same operating conditions were used as discussed above with respect to FIG. 3.

The upper trace 50 is the carbon is region of the XPS spectrum of the PLGA sample on the silicon wafer. The observed peaks are attributable to PLGA, as expected. The lower trace 52 is of the same spectral region after sputtering 200 nm of material away from the surface of the sample with a 12 keV coronene ($C_{24}H_{12}^+$) ion beam. It is clear from a comparison of the two spectra that no significant change in the type and proportion of the chemical state of the carbon atoms of the PLGA has occurred. This result demonstrates that PAHs are efficient at removing material from the surface of a sample without damaging underlying layers. This permits a depth analysis of a sample, whereby layers of material are removed sequentially. It can also be seen from the two spectra of FIG. 4 that no significant deposition of PAH has occurred.

One possible explanation for the unexpectedly good performance of PAHs is that the energy of the primary cluster ion is shared amongst the constituent atoms of the impacting molecule such that while the cluster ion might have an energy of 10 keV each carbon atom in for example coronene would carry a relatively low energy of approximately 400 eV. Therefore the penetration depth into the surface of each impacting atom is low and so the subsurface mixing effects are minimized. This may explain the minimal contamination or false layer deposition observed for PAHs. In this connection, PAHs generally have a compact structure and so minimize the area over which the impact crater extends. However compared to a C60 ion with the same energy per atom, their energy is more evenly spread over the impact area and so there may be a reduced penetration depth. Indeed, molecular dynamics simulations show that in C60 cluster impacts with surfaces the cluster can break into 2 smaller clusters one of which penetrates more deeply into the surface. The more open planar aromatic carbon structure of PAH may mitigate against this deep penetration behaviour.

I claim:

1. An electron spectroscopy apparatus, comprising:
   a high energy particle source for irradiating a sample in an enclosure;
   an electron detector system for detecting electrons emitted from the sample in the enclosure; and
   an ion gun for delivering a polycyclic aromatic hydrocarbon ion beam directly to the sample in the enclosure, wherein the ion gun comprises a polycyclic aromatic hydrocarbon ion source.

2. The electron spectroscopy apparatus according to claim 1, wherein the polycyclic aromatic hydrocarbon is provided in the ion source as a pre-form, powder or fibrous solid.

3. The electron spectroscopy apparatus according to claim 1, wherein the polycyclic aromatic hydrocarbon comprises 5 to 20 aromatic rings.

4. The electron spectroscopy apparatus according to claim 3, wherein the polycyclic aromatic hydrocarbon is coronene.

5. The electron spectroscopy apparatus according to claim 1, wherein the ion gun includes gas supply means to deliver gas to the ioniser.

6. The electron spectroscopy apparatus according to claim 1, wherein the ion gun includes an ion extractor for accelerating ions from the ion source; ion optics for focusing and/or aligning the ions; a mass filter; and an ion separator for removing neutral species.

7. The electron spectroscopy apparatus according to claim 1, wherein the ion gun includes an ion scanner for directing the ions onto different areas of the sample.

8. The electron spectroscopy apparatus according to claim 1, wherein the ion gun is adapted to provide ions of different charge states.

9. The electron spectroscopy apparatus according to claim 1, wherein the electron detector system includes an electron energy analyser, and wherein optionally the electron energy analyser includes a hemispherical analyser and/or a spherical mirror analyser.

10. The electron spectroscopy apparatus according to claim 1, wherein the electron detector system includes a channeltron or microchannel plate electron detector.

11. The electron spectroscopy apparatus according to claim 1, wherein the apparatus includes a vacuum chamber.

12. The electron spectroscopy apparatus according to claim 1, wherein the electron detector system is adapted to detect the kinetic energy and/or the number of electrons.

13. The electron spectroscopy apparatus according to claim 1, wherein the apparatus is an XPS apparatus or a PES apparatus.

14. A polycyclic aromatic hydrocarbon ion gun for use in the apparatus according to claim 1.

15. Use of a polycyclic aromatic hydrocarbon in a method of analysing a sample by electron spectroscopy using the electron spectrometer apparatus of claim 1.

16. An electron spectroscopy apparatus comprising:
a high energy particle source for irradiating a sample;
an electron detector system for detecting electrons emitted from the sample; and
an ion gun for delivering a polycyclic aromatic hydrocarbon ion beam to the sample,
wherein the ion gun comprises a polycyclic aromatic hydrocarbon ion source, and
wherein the ion source comprises:
a gas generator for producing gas phase molecules of the polycyclic aromatic hydrocarbon; and
an ioniser for ionising the gas phase molecules of the polycyclic aromatic hydrocarbon, and
wherein the gas generator comprises a heated chamber which is adapted to operate at a temperature in the range 100° C. to 300° C.

17. The electron spectroscopy apparatus according to claim 16, wherein the ioniser comprises an electron impact ioniser.

18. An electron spectroscopy apparatus comprising:
a high energy particle source for irradiating a sample;
an electron detector system for detecting electrons emitted from the sample; and
an ion gun for delivering a polycyclic aromatic hydrocarbon ion beam to the sample,
wherein the ion gun comprises a polycyclic aromatic hydrocarbon ion source, and
wherein the apparatus further comprises an ion beam controller for switching between first (polycyclic aromatic hydrocarbon) and second (gas) ion beam modes.

19. An electron spectroscopy method, the method including the steps of:
irradiating a sample with high energy particles in an enclosure;
detecting electrons emitted from the sample in the enclosure; and
directing a polycyclic aromatic hydrocarbon ion beam directly onto the sample in the enclosure.

20. The electron spectroscopy method according to claim 17, wherein the polycyclic aromatic hydrocarbon ion beam has an energy of between 2 and 20 keV.

21. The electron spectroscopy method according to claim 19, wherein the method includes the step of removing a surface layer of material from the sample with the polycyclic aromatic hydrocarbon ion beam.

22. The electron spectroscopy method according to claim 19, wherein the method is a sputter depth profiling method.

23. The electron spectroscopy method according to claim 19, wherein the method includes the step of cleaning the surface of a sample with the polycyclic aromatic hydrocarbon ion beam.

24. A method of modifying an electron spectrometer apparatus so that it can perform the method according to claim 19.

* * * * *